United States Patent [19]

Spang et al.

[11] Patent Number: 4,981,975
[45] Date of Patent: Jan. 1, 1991

[54] BENZIMIDAZOLE-2-CARBOXANILIDES

[75] Inventors: Peter Spang, St. Ingbert; Peter Neumann, Mannheim; Hubert Trauth, Dudenhofen, all of Fed. Rep. of Germany

[73] Assignee: BASF Aktiengesellschaft, Ludwigshafen, Fed. Rep. of Germany

[21] Appl. No.: 392,300

[22] Filed: Aug. 11, 1989

[30] Foreign Application Priority Data

Aug. 23, 1988 [DE] Fed. Rep. of Germany ....... 3828535

[51] Int. Cl.$^5$ .................. C07D 235/24; C07D 405/12; C07D 413/06
[52] U.S. Cl. .................................... 548/327; 544/139; 544/370; 546/199; 548/331
[58] Field of Search ................ 544/139, 370; 546/199; 548/327, 331

[56] References Cited

U.S. PATENT DOCUMENTS

| | | | |
|---|---|---|---|
| 3,661,925 | 5/1972 | McCaully et al. | 548/331 |
| 3,740,413 | 6/1973 | McCaully et al. | 548/331 |
| 3,907,700 | 9/1975 | Grier | 252/300 |
| 4,011,236 | 3/1977 | Grier | 548/306 |
| 4,820,757 | 4/1989 | Spang et al. | 548/331 |

Primary Examiner—Robert W. Ramsuer
Attorney, Agent, or Firm—Oblon, Spivak, McClelland, Maier & Neustadt

[57] ABSTRACT

Benzimidazolecarboxanilides of the formula (I)

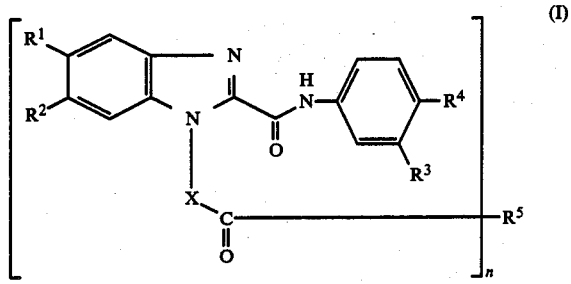

where $R^1$ and $R^2$ are each H, Cl, alkyl, alkoxy, unsubstitued or alkyl- or alkoxy-substituted phenyl or phenylalkyl, $R^3$ and $R^4$ are each H, uninterrupted or —O— interrupted alkyl or alkoxy, unsubstituted or alkyl- or alkoxy-substituted phenyl, phenylalkyl, phenoxy, phenylalkoxy hydroxyalkyl, hydroxyalkoxy, alkylcarbonylamino, alkanoyloxy, benzoylamino or benzoyloxy, X is alkylene, n is 1 or 2 and where—if n is 1—$R^5$ is Cl, —$OR^6$ or —$NR^7R^8$ or—if n is 2—$R^5$ is —O—$R^{12}$—O— or —N($R^9$)—$R^{13}$—N($R^9$)— where $R^6$ is H, unsubstituted, OH— or alkanoyloxy-substituted alkyl whose carbon chain may be interrupted by —O— or —N($R^9$)—, cycloalkyl, alkenyl, phenylalkyl, phenoxyethyl, hydroxy alkyl, phenylhydroxyalkyl or glycidyl, $R^7$ and $R^8$ are H, alkyl, cycloalkyl, phenyl, naphthyl, alkenyl, phenylalkyl, hydroxyalkyl or —$NR^7R^8$, a saturated 5- or 6- membered heterocycle, $R^9$ is alkyl, cycloalkyl, alkenyl, phenyl, naphthyl or phenylalkyl, $R^{12}$ is alkylene, alkenylene, cyclohexylene, oxaalkylene and $R^{13}$ is alkylene, oxaalkylene, diphenylenemethane or dicyclohexylenemethane or —N($R^9$)—$R^{13}$—N($R^9$)— is piperazinylene, are excellent light stabilizers for organic materials such as polymers and coating binders.

4 Claims, No Drawings

BENZIMIDAZOLE-2-CARBOXANILIDES

U.S. Pat. Nos. 3,907,700 and 4,011,236 already disclose benzimidazole-based light stabilizers for plastics. They are N-(benzimidazol-2-yl)phenylcarboxamides of the formula (X)

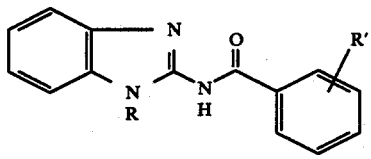

These stabilizers are partly preparable only by complicated methods. In addition, in particularly radiationsensitive plastics, for example polyurethanes, they do not provide sufficient stabilization. Furthermore, these compounds are mostly sparingly soluble and relatively volatile. They tend to crystallize and migrate. These unfavorable properties interfere strongly with their use in plastics and coatings, such as automotive coatings.

To meet present-day requirements, a compound must show excellent compatibility with or high solubility in numerous polymeric substrates and a high thermal stability. In addition, the compound should not escape from the plastics in the course of high-temperature processing. Particularly the development of low-solvent or highsolids coating formulations requires the stabilizers to be highly soluble in the corresponding solvents. Moreover, the use in polyurethanes presupposes a high solubility in particular in the polyetherol or polyesterol components.

The present invention provides compounds of the formula I

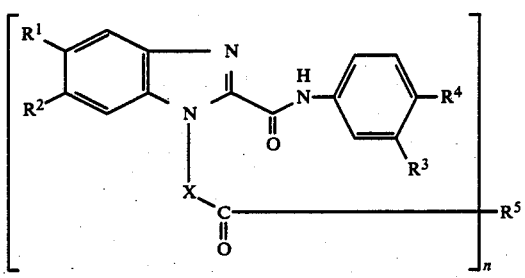

where
$R^1$ and $R^2$ are each independently of the other H, Cl, $C_1$–$C_4$-alkyl, $C_1$–$C_4$-alkoxy, unsubstituted or $C_1$–$C_4$-alkyl- or $C_1$–$C_4$-alkoxy-substituted phenyl or $C_7$–$C_9$-phenalkyl, $R^3$ and $R^4$ are each independently of the other H, $C_1$–$C_{18}$-alkyl, $C_3$–$C_{18}$-alkyl which is interrupted one or more times by —O—, $C_1$–$C_{18}$-alkoxy, $C_4$–$C_{18}$-alkoxy which is interrupted one or more times by —O—, unsubstituted or $C_1$–$C_4$-alkyl- or $C_1$–$C_4$-alkoxy-substituted phenyl, $C_7$–$C_{15}$-phenylalkyl, phenoxy, $C_7$–$C_{15}$-phenylalkyloxy, $C_1$–$C_4$-hydroxyalkyl, $C_1$–$C_4$-hydroxyalkoxy, $C_1$–$C_{12}$-alkylcarbonylamino, $C_1$–$C_{12}$-alkanoyloxy, benzoylamino or benzoyloxy, X is $C_1$–$C_5$-alkylene,
n is 1 or 2 and
$R^5$ is (a) —when n is 1—Cl,

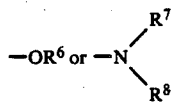

or (b) —when n is 2—a divalent radical of the formula —O—$R^{12}$—O— or

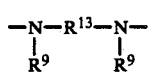

where
$R^6$ is H, unsubstituted or OH-monosubstituted, —disubstituted or -trisubstituted or —O—COR$^9$-substituted $C_1$–$C_{18}$-alkyl, $C_3$–$C_{18}$-alkyl which is interrupted one or more times by —O— or —NR$^9$—, unsubstituted or OH-substituted $C_5$–$C_{12}$-cycloalkyl, unsubstituted or OH-substituted $C_2$–$C_{18}$-alkenyl, $C_7$–$C_{15}$-phenylalkyl, phenoxyethyl,

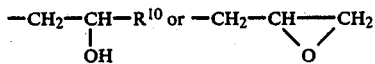

$R^7$ and $R^8$ are each independently of the other H, $C_1$–$C_{18}$-alkyl, $C_3$–$C_{18}$-alkyl which is interrupted one or more times by —O— or —NR$^9$—, $C_5$–$C_{12}$-cycloalkyl, phenyl, naphthyl, $C_3$–$C_{18}$-alkenyl, $C_7$–$C_{15}$-phenylalkyl, $C_2$–$C_4$-hydroxyalkyl or

pyrrolidinyl, piperidinyl, piperazinyl or morpholinyl,
$R^9$ is H, $C_1$–$C_{18}$-alkyl, $C_5$–$C_{12}$-cycloalkyl, $C_3$–$C_8$-alkenyl, phenyl, naphthyl or $C_7$–$C_{18}$-phenylalkyl, is H, $C_1$–$C_{18}$-alkyl, $C_7$–$C_{18}$-phenylalkyl, unsubstituted or substituted phenyl or —CH$_2$OR$^{11}$,
$R^{11}$ is $C_1$–$C_{18}$-alkyl, $C_3$–$C_{18}$-alkenyl, $C_5$–$C_{10}$-cycloalkyl, phenyl or $C_7$–$C_{15}$-phenylalkyl,
$R^{12}$ is $C_2$–$C_8$-alkylene, $C_4$–$C_8$-alkenylene, cyclohexylene, $C_4$–$C_{18}$-alkylene which is interrupted one or more times by —O—,

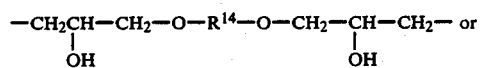

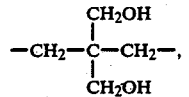

$R^{13}$ is $C_2$–$C_{12}$-alkylene which may be interrupted one or more times by —O—, cyclohexylene,

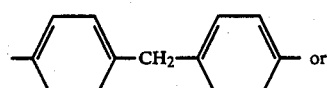

-continued

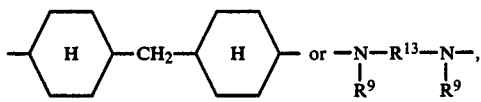

a 2-valent piperazine radical, and $R^{14}$ is $C_2$–$C_8$-alkylene, $C_4$–$C_{18}$-alkylene which is interrupted one or more times by —O—, 1,3- or 1,4-cyclohexylene, 1,3- or 1,4-phenylene,

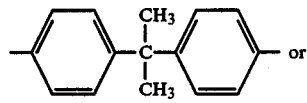

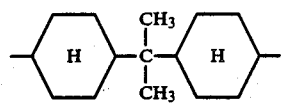

The compounds of the formula (I) according to the invention are effective light stabilizers for organic materials, for example for a large number of polymers. They are incorporated into the polymers in a conventional manner.

The benzimidazole-2-carboxanilides (I) of the invention are readily or very readily soluble in polymers such as plastics and coating binders and accordingly are highly compatible with these media. They are also notable for low volatility and for a low tendency to crystallization. The compounds (I) furthermore are stable at the temperatures required for incorporation.

$R^1$ and $R^2$ are each specifically for example: hydrogen, chlorine, methyl, ethyl, n-propyl, i-propyl, n-butyl, i-butyl, t-butyl, methoxy, ethoxy, propoxy, butoxy, phenyl, benzyl, α-methylbenzyl or α,α-dimethylbenzyl.

Preferably, $R^1$ and $R^2$ are each hydrogen, methyl, methoxy or ethoxy.

$R^3$ and $R^4$ are each preferably hydrogen, $C_1$–$C_{12}$-alkyl, $C_3$–$C_{10}$-alkyl which is interrupted one or more times by —O—, $C_1$–$C_{12}$-alkoxy, $C_4$–$C_{12}$-alkoxy which is interrupted one or more times by —O—, $C_7$–$C_9$-phenylalkyl, phenoxy, $C_7$–$C_9$-phenylalkoxy, $C_7$–$C_{12}$-alkylcarbonylamino, benzoylamino, $C_1$–$C_{12}$-alkanoyloxy or benzoyloxy.

Suitable $R^3$ and $R^4$ together are methylenedioxy and ethylenedioxy.

In addition to the specific substituents mentioned for $R^3$ and $R^4$, they can each also be in particular for example:

(α) $C_1$–$C_{12}$-alkyl such as methyl, ethyl, n-propyl, i-propyl, n-butyl, 2-butyl, tert-butyl, n-pentyl, tert-pentyl, n-hexyl, n-heptyl, n-octyl, 2-ethylhexyl, n-nonyl, n-decyl or n-dodecyl;

(β) $C_1$–$C_{12}$-alkoxy such as methoxy, ethoxy, i-propoxy, n-butoxy, n-pentoxy, i-pentoxy, n-hexoxy, n-heptoxy, n-octoxy, 2-ethylhexoxy, n-nonoxy, n-decoxy or n-dodecoxy;

(γ) phenylalkoxy such as benzyloxy, 2-phenylethoxy or 3-phenylpropoxy.

Particular preference is given to compounds I where $R^3$ is H and
$R^4$ is $C_1$–$C_{12}$-alkyl, $C_1$–$C_{12}$-alkoxy, phenoxy, $C_1$–$C_{12}$-alkylcarbonylamino, benzoylamino or $C_1$–$C_{12}$-alkanoyloxy.

X is preferably methylene, ethylene, n-propylene, n-butylene, n-pentylene, i-propylene, 1-methylpropylene or 1-methylbutylene, in particular methylene, ethylene or propylene.

The meaning of $R^5$ depends on whether n is 1 or 2.

$C_1$–$C_{18}$-Alkyl $R^6$, $R^7$, $R^8$, $R^9$, $R^{10}$ or $R^{11}$ is for example methyl, ethyl, i-propyl, n-butyl, sec-butyl, t-butyl, t-amyl, n-hexyl, 2-ethylhexyl, n-octyl, 1,1,3,3-tetramethylbutyl, n-decyl, n-dodecyl, 1,1,7,7-tetramethyloctyl or n-octadecyl.

$C_5$–$C_{12}$-Cycloalkyl $R^6$, $R^7$, $R^8$, $R^9$ or $R^{11}$ is for example: cyclopentyl, cyclohexyl, cycloheptyl, cyclooctyl or cyclodecyl. Cycloalkyl $R^6$ can also be OH-substituted.

Alkenyl $R^7$, $R^8$ or $R^9$ is for example: allyl, methallyl, 2-n-hexenyl, 4-n-octenyl, oleyl or decenyl.

Alkenyl $R^6$ is for example alkenyl as mentioned for $R^7$, $R^8$ and $R^9$, vinyl, 10-n-undecenyl or 9-n-octadecenyl, which may all also be OH-substituted.

$C_3$–$C_{18}$-Alkyl $R^6$, $R^7$ or $R^8$ which is interrupted by —O— or —$NR^9$— and may be OH-substituted is specifically for example: methyloxyethyl, ethoxyethyl, butoxyethyl, butoxypropyl, $CH_3OCH_2CH_2OCH_2CH_2$—, $CH_3CH_2OCH_2CH_2OCH_2CH_2$—, $C_4H_9OCH_2CH_2OCH_2CH_2$—, dodecyloxypropyl, 2-hydroxyethyl, 2-hydroxypropyl, 4-hydroxybutyl, 6-hydroxyhexyl, —$CH_2CH_2$—NH—$C_4H_6$,—$CH_2CH_2CH_2$—NH—$C_8H_{17}$,

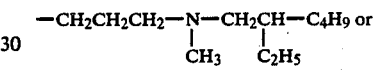

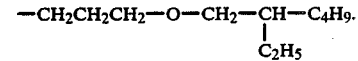

$R^6$ can also be phenoxyethyl.

$C_2$–$C_4$-Hydroxyalkyl $R^7$ or $R^8$ can be hydroxyethyl, hydroxypropyl or hydroxybutyl.

$C_7$–$C_{15}$-Phenylalkyl $R^7$ or $R^8$ can be for example benzyl, 1-phenylethyl, 2-phenylethyl, 1-phenylpropyl or α,60 -dimethylbenzyl.

Phenylalkyl $R^6$, $R^9$, $R^{10}$ or $R^{11}$ is a radical as mentioned for $R^7$ and $R^8$, these radicals being identical or different.

$R^7$, $R^8$ and $R^9$ can each also be phenyl, α-naphthyl or β-naphthyl.

$C_2$–$C_8$-Alkylene $R^{12}$ or $R^{14}$ is for example ethylene, propylene, butylene, hexylene or octylene.

$C_2$–$C_{12}$-Alkylene $R^{13}$ is for example alkylene as mentioned for $R^{12}$ and $R^{14}$, decylene or dodecylene.

$C_4$–$C_8$-Alkenylene $R^{12}$ is for example butenylene.

$C_4$–$C_{18}$-Alkylene $R^{12}$ or $R^{14}$ interrupted by —O— is for example:

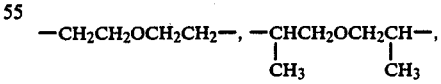

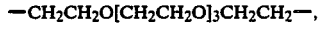

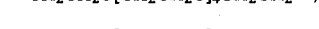

-continued

—CH$_2$CH$_2$O[CH$_2$CH$_2$O]$_7$CH$_2$CH$_2$—.

Particular preference is given to compounds of the formula (I) where R$^1$, R$^2$, R$^3$, R$^4$ and X are each as preferred above, n is 1 and R$^5$ is

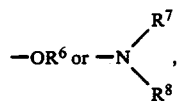

where R$^6$ is straight-chain or branched C$_1$–C$_{12}$-alkyl, straight-chain or branched C$_3$–C$_{18}$-alkyl which is interrupted by —O—, phenoxyethyl, cyclohexyl or

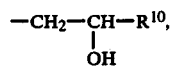

R$^7$ and R$^8$ are each independently of the other straight-chain or branched C$_1$–C$_{12}$-alkyl, straight-chain or branched C$_3$–C$_{18}$-alkyl interrupted by —O—, or cyclohexyl, R$^{10}$ is straight-chain or branched C$_1$–C$_{12}$-alkyl or —CH$_2$OR$^{11}$ and R$^{11}$ is straight-chain or branched C$_1$–C$_{12}$ -alkyl or cyclohexyl.

Particular preference is further given to those compounds of the formula (I) where R$^1$, R$^2$, R$^3$, R$^4$ and X are as preferred above, n is 2 and R$^5$ is a divalent radical of the formula —O—R$^{12}$—O— or

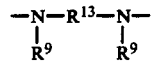

where R$^9$ is H or C$_1$–C$_8$-alkyl, R$^{12}$ is C$_2$–C$_6$-alkylene, C$_4$–C$_{10}$-alkylene which is interrupted by —O— or

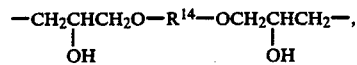

R$^{13}$ is straight-chain or branched C$_2$–C$_{12}$-alkylene and R$^{14}$ is C$_2$–C$_6$-alkylene or C$_4$–C$_{10}$-alkylene interrupted by —O—, said alkylenes being linear or branched.

To prepare the compounds of the formula (I) according to the invention, it is preferable to start from benzimidazole-2-carboxanilides of the formula (II) whose preparation is described for example in EP-A-No. 0,284,828.

The benzimidazolecarboxylic acids of the formula (I) where R$^6$=H can be synthesized by route (a) by reaction with haloalkylenecarboxylic acids of the formula (III) or by route (b) by reaction with lactones of the formula (IV) where X is for example C$_2$–C$_5$-alkylene such as ethylene, propylene, butylene or pentylene.

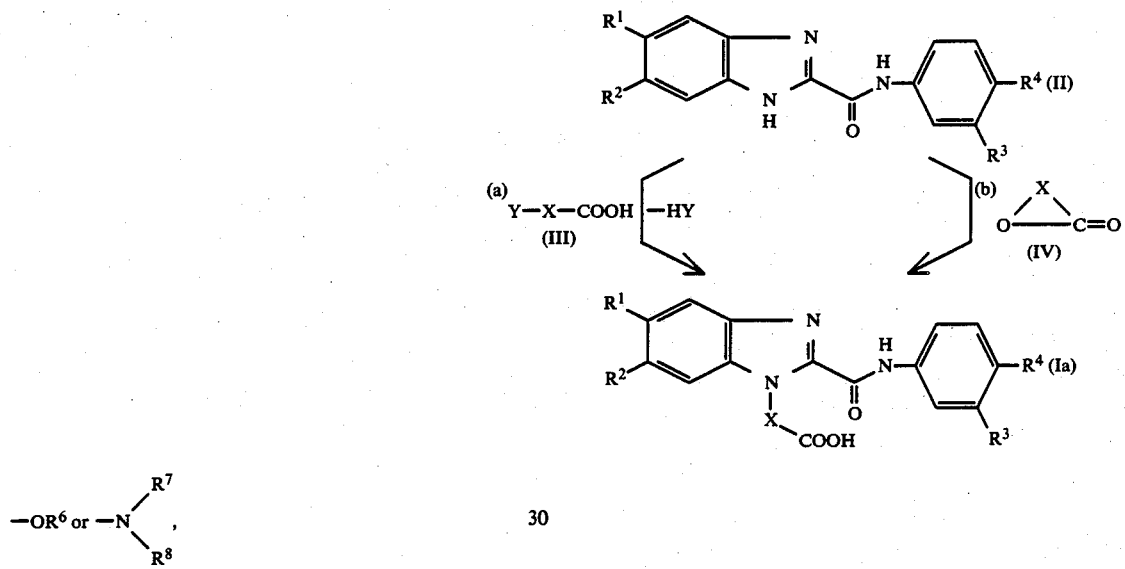

The radical Y is preferably Br or Cl, in particular Cl. The reactions by (a) are preferably carried out in inert solvents such as dimethylformamide, dimethylacetamide, N-methylpyrrolidone or ethylene glycol diethers in the presence of an auxiliary base, such as K$_2$CO$_3$, Na$_2$CO$_3$, KHCO$_3$ or NaHCO$_3$, at from 60° to 140° C., preferably at from to 120° C.

The reaction by (b) is preferably carried out in an excess of lactone (IV) in the presence of basic compounds, such as NaOH, KOH, Na$_2$CO$_3$ or K$_2$CO$_3$, at from 150° to 200° C.

The benzimidazolecarboxylic acids (Ia) obtainable by the above methods are convertible into compounds (I) where R$^6$≠H by the following methods:

(1) Esterification of the carboxylic acid (Ia) with alcohols of the formula R$^6$OH, excluding the radical

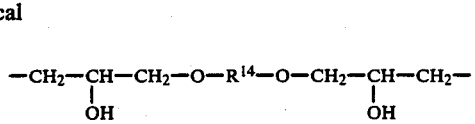

in the presence of thionyl chloride to obtain compounds (I) where n=1.

Using diols HO—R$^{12}$—OH with R$^{12}$ other than the radical

—CH$_2$—CH—CH$_2$—O—R$^{14}$—O—CH$_2$—CH—CH$_2$—
　　　|　　　　　　　　　　　　　　|
　　　OH　　　　　　　　　　　　　OH gives compounds (I) where n=2.

(2) Reaction of benzimidazolecarboxylic acids (Ia) with an epoxy (V) in accordance with the following formula scheme:

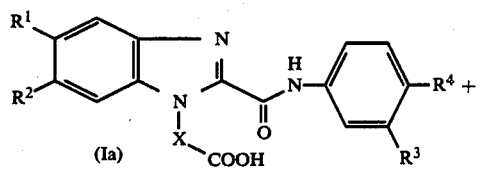

(Ia)

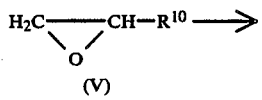

(V)

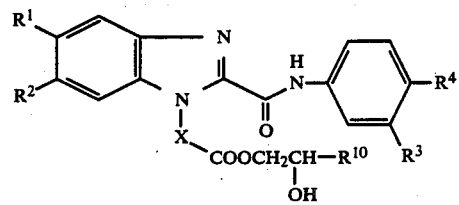

(3) Conversion of the benzimidazolecarboxylic acids (Ia) into the acyl chlorides of the formula I ($R^5=Cl$, n=1) in a conventional manner. To this end, the corresponding benzimidazolecarboxylic acid (Ia) is suspended, for example in toluene, in the presence of a catalytic amount of dimethylformamide, 2.5 times the excess of thionyl chloride are added, and the mixture is stirred at 80° C. until the reaction has ended. The acyl chloride precipitates and is filtered off with suction and washed with naphtha.

Possible starting compounds for the preparation of further compounds (I) are the alkyl benzimidazole-1-carboxylates likewise obtainable by (1), in particular those with low molecular weight alkyl groups, such as methyl and ethyl, which can also be prepared by the following methods:

(1a) Reaction of benzimidazole-2-carboxanilides (II) with haloalkylenecarboxylic esters of the formula (VI)

$$Y-X-COOR^6 \qquad (VI)$$

or if $X=-CH_2CH_2-$ by reacting alkyl acrylates of the formula (VII)

$$H_2C=CH-COOR^6 \qquad (VII)$$

The low molecular weight benzimidazole-1-carboxylic esters (I) thus obtainable can be further reacted by the following methods:

(4) Transesterification of the methyl benzimidazole-1-carboxylates (I) obtainable by (1) or (1a) in the case of n=1 with alcohols of the formula $R^6$—OH in the presence of a transesterification catalyst such as tetrabutyl orthotitanate, lithium amide, sodium methoxide or p-toluenesulfonic acid, by distilling off the methanol formed. This gives higher molecular weight benzimidazole-1-carboxylic esters (I).

In the same way it is also possible to carry out transesterifications of the esters (I) obtainable by (1) or (1a) with diols of the formula HO—$R^{12}$—OH to obtain compounds (I) where n=2. The molar amount of diol is cut by half in accordance with the reaction equation.

To prepare the benzimidazole-1-carboximides of the formula I, the procedure is as follows:

(5) Reaction of benzimidazole-1-carboxylic esters, preferably methyl or ethyl esters, with ammonia or a primary or secondary amine of the formula

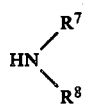

or with diamines of the formula

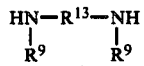

in the presence or absence of catalysts, for example lithium amide or sodium methoxide, in each case by distilling off the liberated alcohol. In the former case, the product obtained is (I) where n=1 and in the latter case it is (I) where n=2.

A further method to prepare benzimidazole-1-carboxamides comprises reacting benzimidazole-2-carboxanilides (II) with a halocarboxamide of the formula (VIII)

or with a dicarboxamide of the formula (IX)

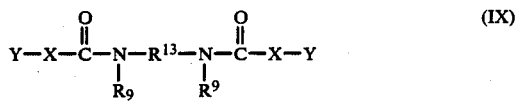

Using (VIII) gives compounds (I) where n=1 and using (IX) gives compounds (I) where n=2.

The amides of the formulae (VIII) and (IX) can be prepared in a conventional manner, for example by reacting the corresponding halocarbonyl chlorides with the above-described primary or secondary mono- or diamines.

(6) The benzimidazole-1-carboxylic acids (Ia) can be incorporated into PES resins or epoxy resins and attached therein via binders present in the coating. The incorporation is possible not only in the course of the preparation of the resins but also in the course of the chemical crosslinking of the coating resins during baking.

Incorporation can be effected for example by mixing compounds (I) with or without further additives into the melt by customary methods before or during molding, or else by applying the dissolved or dispersed compounds to the polymer directly or by mixing into a solution, suspension or emulsion of the polymer, the solvent being subsequently removable if necessary, for example by evaporation.

Suitable polymers are for example: polyolefins, polystyrene, styrene polymers, halogen-containing vinyl polymers, polyacrylates, polymethacrylates, polyacrylamides, polyacrylonitrile, polyvinyl alcohol and acyl derivatives thereof, polyacetates, polyalkylene oxides, polyphenylene oxides, polyurethanes, polyureas, polysulfones, polyamides, polyesters, polycarbonates, crosslinked polymers from aldehydes and phenols, ureas or melamine, unsaturated polyester resins, alkyd resins and thermosetting and thermoplastic acrylic resins.

The present invention thus also provides stabilized organic materials, in particular synthetic polymers, which contain from 0.05 to 10, preferably from 0.1 to 5, by weight of one or more compounds of the formula (I) (based on the organic material).

The compounds according to the invention not only are effective light stabilizers but, owing to their low volatility at high temperatures, they are also highly suitable for stabilizing polymers which need to be processed at high temperatures.

The compounds (I) according to the invention are accordingly highly suitable for stabilizing polyesters such as polyethylene terephthalate, polybutylene terephthalate and copolymers thereof, polyamides, for example nylon-6, nylon-6,6, nylon-6,10, etc., copolymers of MF and UF-resins, hot-crosslinkable and thermoplastic acrylic resins, and polyurethanes.

Compounds (I) are very particularly suitable for stabilizing coating formulations which contain such polymers.

The materials stabilized with (I) can be converted in a conventional manner into the forms customary for use, for example into films, fibers, ribbons or profiles, or be used as binders for coatings, adhesives, cements or molding compositions.

In practice, the compounds of the formula I can be used together with from 0.1 to 5, preferably from 0.5 to 3, % by weight of further customary additives, such as antioxidants, further light stabilizers or mixtures thereof.

Such customary additives are for example: antioxidants, UV absorbers and light stabilizers such as 2-(2'-hydroxyphenyl)-benzotriazoles, 2,4-bis(2'-hydroxyphenyl) 6-alkyl-s-triazine, 2-hydroxybenzophenones, 1,3-bis(2'-hydroxybenzoyl)benzenes, esters of substituted or unsubstituted benzoic acids, acrylates, also nickel compounds, sterically hindered amines, metal deactivators, phosphites, peroxide-destroying compounds, polyamide stabilizers, basic costabilizers, nucleating agents and other additives such as plasticizers, lubricants, emulsifiers, fillers, carbon black, kaolin, talc, glass fibers, pigments, fluorescent brightening agents, flame-proofing agents and antistats.

The compounds of the formula (I) are also highly suitable for protecting ABS polymers and in particular polyurethanes derived from polyethers, polyesters and polybutadiene having terminal hydroxyl groups and aliphatic or aromatic polyisocyanates, and intermediates therefor, against degradation by heat and in particular by the action of light.

An improved stabilizing effect is obtained on using in addition a known antioxidant, for example a compound based on sterically hindered phenols or a sulfur- or phosphorus-containing costabilizer.

Suitable phenolic antioxidants of this type are for example 2,6-di-tert-butyl-4-methylphenol, n-octadecyl β-(3,5-di-tert-butyl-4-hydroxyphenyl)propionate, 1,1,3-tris(2-methyl-4-hydroxy-5-tert-butylphenyl)butane, 1,3,5-trimethyl-2,4,6-tris(3,5-di-tert-butyl-4-hydroxybenzyl)benzene, 1,3,5-tris(3,5-di-tert-butyl-4-hydroxybenzyl) isocyanurate, 1,3,5-tris[3,5-di-tert-butyl-4-hydroxyphenylpropionyloxyethyl]isocyanurate, 1,3,5tris(2,6-di-methyl-3-hydroxy-4-tert-butylbenzyl) isocyanurate and pentaerythritol tetrakis[β-(3,5-di-tert-butyl-4-hydroxyphenyl)propionate].

Suitable phosphorus-containing antioxidants are for example: tris(nonylphenyl) phosphite, distearyl pentaerythritol diphosphite, tris(2,4-di-tert-butylphenyl) phosphite, tris(2-tert-butyl-4-methylphenyl) phosphite, bis(2,4-di-tert-butylphenyl) pentaerythritol diphosphite and tetrakis(2,4-di-tert-butylphenyl)-4,4'-biphenylene diphosphite.

Suitable sulfur-containing antioxidants are for example dilauryl thiodipropionate, dimyristyl thiodipropionate, distearyl thiodipropionate, pentaerythritol tetrakis (β-laurylthiopropionate) and pentaerythritol tetrakis(β-hexylthiopropionate).

Particularly good stabilization is obtained on adding to the compounds of the formulae (I) at least one light stabilizer of the class of sterically hindered amines in a customary concentration.

Suitable sterically hindered amines are for example: bis(2,2,6,6-tetramethylpiperidyl) sebacate, bis(1,2,2,6,6-pentamethylpiperidyl) sebacate, the condensation product of 1-hydroxyethyl-2,2,6,6-tetramethyl-4-hydroxypiperidine and succinic acid, the condensation product of N,N'-(2,2,6,6-tetramethylpiperidyl)hexamethylenediamine and 4-tert-octylamino-2,6-dichloro-1,3,5-s-triazine, tris(2,2,6,6-tetramethylpiperidyl) nitrilotriacetate, tetrakis(2,2,6,6-tetramethyl-4-piperidyl)-1,2,3,4-butanetetracarboxylic acid, 1,1'-(1,2-ethanediyl)-bis(3,3,5,5-tetramethylpiperazinone), and the condensation products of 4-amino-2,2,6,6-tetramethylpiperidines and tetramethylolacetylenediureas.

Particularly good stabilization of polyurethanes is obtained on stabilizing the polyurethane with a mixture of one or more compounds of the formula (I), one or more of the abovementioned antioxidants, and one or more sterically hindered amine compounds.

The sparing volatility, in particular if combined with good substrate compatibility and solubility, makes it possible to incorporate the compounds according to the invention into polymers without problems, the polymers still showing excellent stability even after processing at elevated temperatures.

The high substrate compatibility of the compounds (I) according to the invention together with the abovementioned sparing volatility permit the processing and use of the stabilized products at higher temperatures and an extended use period of the products at customary temperatures. These properties prevent the undesirable exudation of the stabilizer during processing, which otherwise frequently causes damage to the production equipment.

The Examples which follow additionally illustrate the invention.

(A) Preparation Examples

EXAMPLE 1

112.4 g (0.4 mol) of 4'-ethoxybenzimidazole-2-carboxanilide and 165.6 g of K₂CO₃ are suspended in 600 ml of dimethylformamide, and the suspension is heated to 95°–100° C. At that temperature, 57 g of chloroacetic acid are added to the reaction mixture a little at a time in the course of 150 minutes, and the resulting mixture is stirred for a further 5 hours. To work up the reaction mixture, it is poured into 3 l of water. The pH is adjusted to 11 by adding K₂CO₃, undissolved matter is filtered off, and the filtrate is acidified down to pH 1 by adding concentrated hydrochloric acid. The precipitated product is filtered off with suction and thoroughly washed with water, leaving 78.4 g of a pale yellow solid of the formula

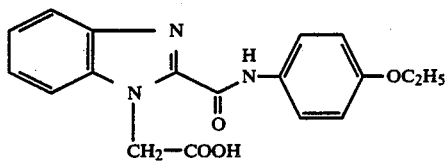

having a melting point of 234°-236° C. (dec.).
Analysis: $C_{18}H_{17}N_3O_4$ (339.4).
Calculated: C 63.72; H 5.02; N 12.39; O 18.87, Found: C 63.4; H 5.1; N 12.2; O 18.7.

EXAMPLE 2

Example 1 is repeated, except that chloropropionic acid is used in place of chloroacetic acid, affording the corresponding benzimidazole-N-propionic acid of the formula

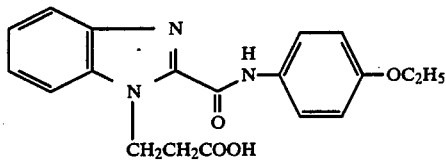

having a melting point of 205° C. (dec.).

EXAMPLE 3

140.5 g (0.5 mol) of 4'-ethoxybenzimidazole-2-carboxanilide and 82.8 g of $K_2CO_3$ are suspended in 600 ml of γ-butyrolactone, and the suspension is stirred at 150° C. for 4 hours. It is then poured into 4 l of water, active charcoal is added, and the mixture is subsequently stirred for 1 hour. After filtration, ice and concentrated hydrochloric acid (pH 2-3) are added to the filtrate to precipitate the carboxylic acid, which is filtered off with suction and washed with water, leaving 162 g of a colorless product of the formula

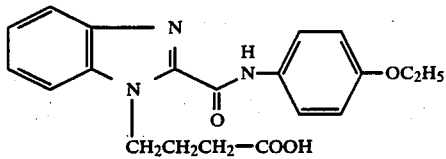

of melting point 172°-175° C.
Analysis: $C_{20}H_{21}N_3O_4$ (367.4).
Calculated: C 65.39; H 5.73; N 11.44; O 17.44, Found: C 64.7; H 5.9; N 10.9; O 18.3.

EXAMPLE 4

338 g of a 4'-ethoxybenzimidazole-2-carboxanilide, 200 g of $K_2CO_3$ and 174 g of methyl chloroacetate in 800 ml of dimethylformamide are heated with stirring at 90°-95° C. for 75 minutes. The reaction mixture is then filtered hot with suction, and the filter residue is washed with about 200 ml of hot dimethylformamide. The solution obtained is treated with active charcoal and stirred into 10 l of methanol. The resulting precipitate is filtered off with suction washed with methanol and dried at 80° C., leaving 258 g of methyl ester of the formula

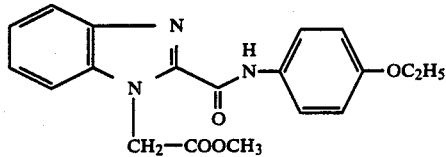

having a melting point of 140°-141° C.
Analysis: $C_{19}H_{19}N_3O_4$ (353.4).
Calculated: C 64.58; H 5.39; N 11.90; O 18.13, Found: C 64.6; H 5.6; N 11.9; O 18.0.

EXAMPLE 5

169 g of 4'-ethoxybenzimidazole-2-carboxanilide, 100 g of $K_2CO_3$ and 98 g of methyl chloropropionate in 500 ml of dimethylformamide are heated at 90°-95° C. for 3.5 hours. The mixture is worked up as described in Example 4. The product is precipitated into 4 l of methanol in the presence of 1 kg of ice. Filtration with suction, washing and drying leaves 188.1 g of a colorless solid of the formula

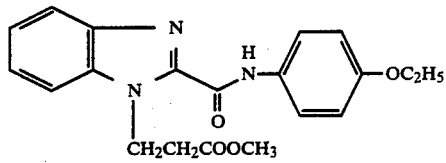

having a melting point of 121°-122° C.
Analysis: $C_{20}H_{21}N_3O_4$ (367.4).
Calculated: C 65.39; H 5.73; N 11.44; O 17.44, Found: C 65.5; H 5.8; N 11.3; O 17.5.

EXAMPLE 6

Example 5 is repeated using methyl chlorobutyrate in place of methyl chloropropionate. This gives the methyl ester of benzimidazole-N-butyric acid, of the formula

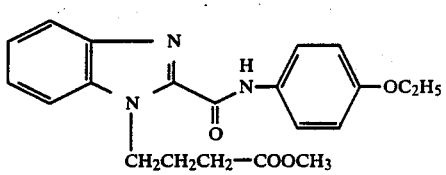

having a melting point of 110°-111° C.
Analysis: $C_{21}H_{23}N_3O_4$ (381.4). Calculated: C 66.14; H 6.04; N 11.02; O 16.80, Found: C 65.8; H 6.1; N 11.1 O 16.8.

EXAMPLES 7-14

The methods described in Examples 4 and 5 were used to prepare the benzimidazole-1-carboxylic esters listed in Table 1.

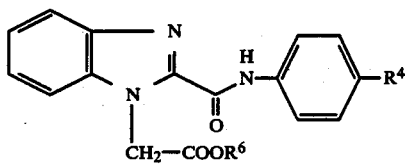

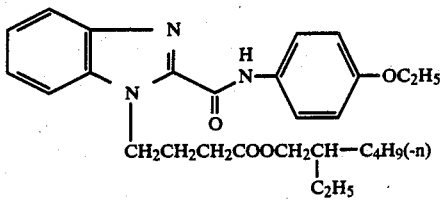

TABLE 1

| Ex. | R⁴ | R⁶ | mp [°C.] | | Analysis | | | |
|---|---|---|---|---|---|---|---|---|
| | | | | | C | H | N | O |
| 7 | H | $C_2H_5$ | 136–8 | calc. | 66.87 | 5.27 | 13.0 | 14.36 |
| | | | | found | 67.2 | 5.5 | 12.9 | 14.5 |
| 8 | $OCH_3$ | $CH_3$ | 170–1 | calc. | 63.72 | 5.02 | 12.38 | 18.88 |
| | | | | found | 63.5 | 5.2 | 12.5 | 18.5 |
| 9 | $OC_2H_5$ | $C_2H_5$ | 132–3 | calc. | 65.39 | 5.73 | 11.44 | 17.44 |
| | | | | found | 65.3 | 5.9 | 11.5 | 17.4 |
| 10 | $OC_2H_5$ | $t\text{-}C_4H_9$ | 145–8 | calc. | 66.83 | 6.34 | 10.63 | 16.20 |
| | | | | found | 67.1 | 6.4 | 10.4 | 16.0 |
| 11 | $OC_2H_5$ | $n\text{-}C_{12}H_{25}$ | 88–90 | calc. | 70.96 | 8.14 | 8.28 | 12.62 |
| | | | | found | 70.9 | 8.3 | 8.1 | 12.4 |
| 12 | $OC_2H_5$ | $n\text{-}C_{16}H_{33}$ | 82–83 | calc. | 72.41 | 8.76 | 7.46 | 11.36 |
| | | | | found | 72.7 | 8.8 | 7.3 | 11.4 |
| 13 | $OC_2H_5$ | $n\text{-}C_{18}H_{37}$ | 82 | calc. | 73.09 | 9.04 | 7.11 | 10.82 |
| | | | | found | 72.9 | 9.3 | 6.6 | 11.2 |
| 14 | $NHCOCH(C_2H_5)C_4H_9$ | $t\text{-}C_4H_9$ | 62–5 | calc. | 68.25 | 7.37 | 11.38 | 13.00 |
| | | | | found | 68.1 | 7.4 | 11.6 | 13.4 |

EXAMPLE 15

36.7 g of 1-(3-carboxypropyl)-4'-ethoxybenzimidazole-2-carboxanilide (compound of Example 3) are suspended in 400 ml of absolute ethanol. 13.1 g of thionyl chloride are added dropwise at from −5° to 0° C., and the reaction mixture is stirred at room temperature for 2 hours and at 40°–45° C. for a further 4 hours. It is then poured onto 1 l of ice-water and neutralized with NaHCO₃. The precipitated solid is filtered off with suction and throughly washed with water, leaving 37.6 g of the ethyl ester of the formula

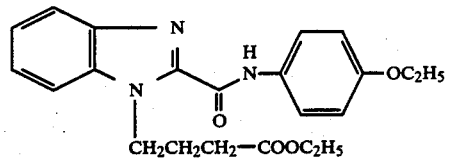

of melting point 94°–95° C.

EXAMPLE 16

13.1 g of thionyl chloride were added dropwise with ice-cooling to a suspension of 36.7 g of 1-(3-carboxypropyl)-4'-ethoxybenzimidazole-2-carboxanilide in 300 ml of 2-ethylhexanol. The reaction mixture is stirred at room temperature for 2 hours and at 50°–55° C. for 4 hours. The suspension is filtered with suction, and the filter residue is washed with naphtha and dissolved in 500 ml of ethyl acetate. The solution is washed with a saturated NaHCO₃ solution and twice with about 500 ml of water, dried over Na₂SO₄ and then purified with active charcoal and bleaching earth. The solvent is distilled off, leaving 41.0 g of a colorless product of the formula

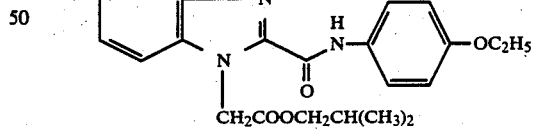

of melting point 56°–60° C.

Analysis: $C_{28}H_{37}N_3O_4$ (395.5). Calculated: C 70.14; H 7.73; N 8.77; O 13.36, Found: C 70.3; H 7.9; N 8.5; O 13.4.

EXAMPLE 17

17.7 g of 1-carbomethoxymethyl-4'-ethoxybenzimidazole-2-carboxanilide (compound of Example 4) in 100 ml of isobutanol are heated in the presence of 0.4 g of sodium methoxide at 100°–105° C. for 2 hours. Excess isobutanol is drawn off under reduced pressure, and the residue is stirred up in water and filtered off with suction. The solid obtained is dissolved in 400 ml of acetone, and the solution is purified with active charcoal and poured onto 1.5 l of ice-water. Filtering off with suction, washing and drying leaves 13.5 g of a colorless product of the formula having a melting point of 80°–84° C.

Analysis $C_{22}H_{25}N_3O_4$ (395.5). Calculated: C 66.8; H 6.33; N 10.63; O 16.21, Found: C 66.8; H 6.5; N 10.7; O 16.0.

EXAMPLE 18

17.7 g of 1-carbomethoxymethyl-4'-ethoxybenzimidazole-2-carboxanilide (compound of Example 4) are heated at 120°–125° C. together with 80 ml of 1-octanol and 6 g of p-toluenesulfonic acid for 7.5 hours. The reaction mixture is taken up in 300 ml of toluene and extracted three times with 800 ml of water, and the toluene phase is dried over Na₂SO₄. After purification with active charcoal and bleaching earth, the solvent and excess alcohol are distilled off under reduced pressure, leaving 21.2 g of a slightly yellow oil of the formula

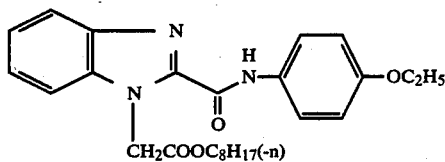

which solidifies as a wax on prolonged standing (melting point: 80°–81° C.).

Analysis: $C_{26}H_{33}N_3O_4$ (451.6). Calculated: C 69.18; H 7.32; N 9.31; O 14.19, Found: C 69.1; H 7.2; N 8.9; O 14.0.

EXAMPLES 19-23

The method of Example 18 was used to prepare the following esters according to the invention by transesterifying the corresponding methyl benzimidazole-1-carboxylates with the corresponding alcohols:

EXAMPLE 19

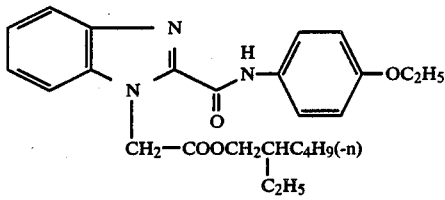

Colorless wax melting point: 48°–51° C.

Analysis: $C_{26}H_{33}N_3O_4$ (451.6). Calculated: C 69.18; H 7.32; N 9.31; O 14.19, Found: C 69.2; H 7.5; N 8.7; O 14.0.

EXAMPLE 20

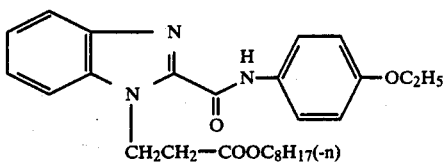

Melting point: 77°–79° C.

Analysis: $C_{27}H_{35}N_3O_4$ (465.7). Calculated: C 69.67; H 7.53; N 9.0; O 13.77. Found: C 69.4; H 7.7; N 8.8; O 13.6.

EXAMPLE 21

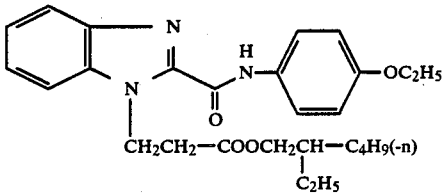

Melting point: 67°–69° C.

Analysis $C_{27}H_{35}N_3O_4$ (465.7).

Calculated: C 69.67; H 7.53; N 9.03; O 13.77. Found: C 69.5; H 7.7; N 8.9; O 14.0.

EXAMPLE 22

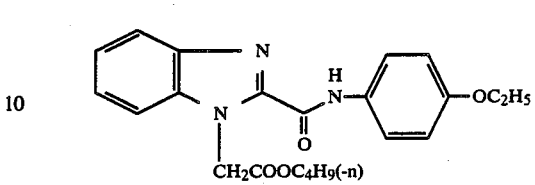

Melting point: 108°–109° C.

Analysis: $C_{22}H_{25}N_3O_4$ (395.5).

Calculated: C 66.82; H 6.37; N 10.63; O 16.18. Found: C 66.9; H 6.4; N 10.60 16.0.

EXAMPLE 23

Alcohol used = 1:1 mixture of isobutanol and n-butanol

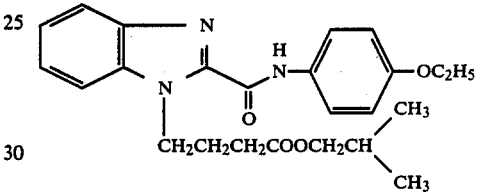

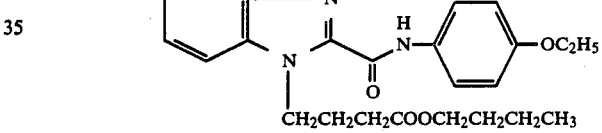

1:1 mixture ($^1$H-NMR analysis)

Analysis: $C_{24}H_{29}N_3O_4$ (423.6).

Calculated: C 68.08; H 6.86; N 9.93; O 15.13. Found: C 68.0; H 7.0; N 9.9; O 15.1.

EXAMPLE 24

17.7 g of 1-carbomethoxymethyl-4'-ethoxybenzimidazole-2-carboxanilide and 6 g of p-toluenesulfonic acid in 60 ml of benzyl alcohol are heated at 135°–140° C. for 4 hours. The reaction mixture is cooled down to 50° C. and poured into about 500 ml of methanol. The benzyl ester is precipitated by a gradual addition of 2540 ml of ice-water, and is subsequently stirred for minutes. The colorless product is filtered off with suction and washed with methanol and naphtha, leaving 16.3 g of solid of the formula

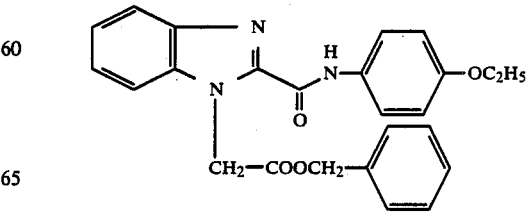

of melting point: 130°–131° C.

Analysis: $C_{25}H_{23}N_3O_4$ (429.6). Calculated: C 69.93; H 5.37; N 9.79; O 14.91, Found: C 70.1; H 5.6; N 9.7; O 14.5.

EXAMPLES 25-29

The method described in Example 24 is used on 2-phenylethanol, 2-phenoxyethanol, ethylene glycol ethyl ether, diethylene glycol methyl ether and diethylene glycol butyl ether to prepare the following benzimidazole-1-carboxylic esters according to the invention:

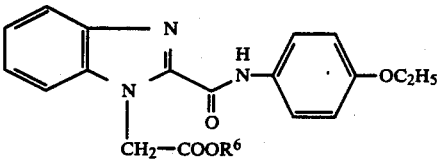

| Ex. | $R^6$ | mp [°C.] | | C | H | N | O |
|---|---|---|---|---|---|---|---|
| | | | Analysis | | | | |
| 25 | CH₂CH₂—C₆H₅ | 128 | calc. | 70.43 | 5.65 | 9.48 | 14.44 |
| | | | found | 70.7 | 5.7 | 9.6 | 14.3 |
| 26 | CH₂CH₂—O—C₆H₅ | 99-100 | calc. | 67.97 | 5.45 | 9.15 | 17.43 |
| | | | found | 67.9 | 5.7 | 9.2 | 17.9 |
| 27 | $CH_2CH_2OC_2H_5$ | 88-90 | calc. | 64.23 | 6.09 | 10.22 | 19.46 |
| | | | found | 64.6 | 6.2 | 10.0 | 19.5 |
| 28 | $CH_2CH_2OCH_2CH_2OCH_3$ | 98-99 | calc. | 62.58 | 6.13 | 9.52 | 21.77 |
| | | | found | 62.7 | 6.3 | 9.5 | 21.5 |
| 29 | $CH_2CH_2OCH_2CH_2OC_4H_9(-n)$ | 53 | calc. | 64.6 | 6.84 | 8.69 | 19.87 |
| | | | found | 64.3 | 7.1 | 8.6 | 19.9 |

EXAMPLE 30

17.0 g of 1-carboxymethyl-4'-ethoxybenzimidazole-2-carboxanilide (from Example 1) and 2.7 g of diethylene glycol are refluxed in 200 ml of toluene in the presence of 5 g of p-toluenesulfonic acid for 16 hours. The solvent is distilled off under reduced pressure, and the residue is dissolved in 500 ml of methanol by heating and purified with active charcoal. 400 ml of ice-water are added to precipitate the product, which is filtered off with suction and washed with water, leaving 10.5 g of a slightly yellow product of the formula

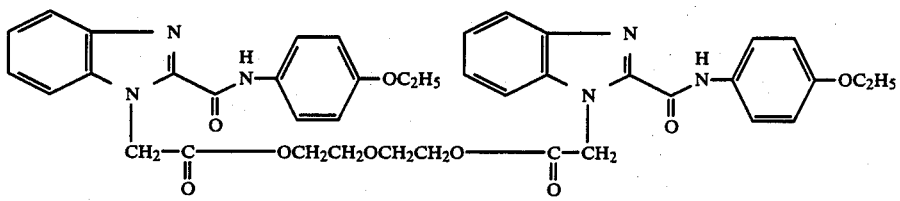

of melting point 160° C.
Analysis: $C_{40}H_{40}N_6O_9$ (748.9).
Calculated: C 64.1; H 5.3; N 11.23; O 19.23, Found: C 63.9; H 5.4; N 11.3; O 19.1.

EXAMPLE 31

38.1 g of 1-carbomethoxypropyl-4'-ethoxybenzimidazole-2-carboxanilide (compound of Example 6) and 12 g of p-toluenesulfonic acid in 100 ml of triethylene glycol are heated at 140°–145° C. for 4.5 hours. The reaction mixture is then poured onto 1 l of ice-water, and the aqueous phase is extracted twice with 500 ml of ethyl acetate. The organic phase is washed with water, dried over $Na_2SO_4$ and purified with active charcoal. The solvent is distilled off under reduced pressure to leave 41 g of a product of the formula

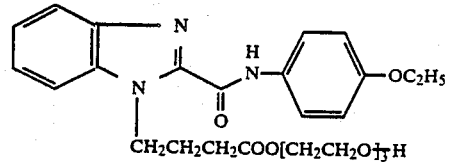

in the form of a pale yellow oil.
Analysis: $C_{26}H_{33}N_3O_7$ (499.6).
Calculated: C 62.52; H 6.62; N 8.42; O 22.44, Found: C 62.7; H 6.7; N 8.4; O 22.5.

EXAMPLES 32-36

The method of Example 31 is employed to transesterify the corresponding methyl benzimidazolecarboxylates with polyglycols and glycol ethers to prepare the following higher molecular weight benzimidazole-1-carboxylic esters:

EXAMPLE 32

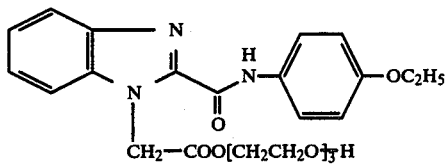

pale yellow resin.

Analysis: $C_{24}H_{29}N_3O_7$ (471.5).
Calculated: C 61.14; H 6.17; N 8.91; O 23.78, Found: C 61.1; H 6.2; N 9.0; O 23.9.

EXAMPLE 33

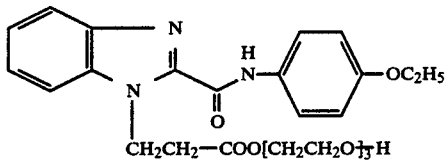

yellowish oil

Analysis: $C_{25}H_{21}N_3O_7$ (485.5).
UV($CH_2Cl_2$): $\lambda_{max}$ ($\epsilon \cdot 10^{-3}$) = 312 nm (22.4).

EXAMPLE 34

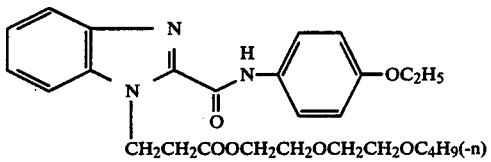

yellowish oil

Analysis: $C_{27}H_{35}N_3O_6$ (497.6).
UV($CH_2Cl_2$): $\lambda_{max}$ ($\epsilon \cdot 10^{-3}$) = 312 nm (21.6).

EXAMPLE 35

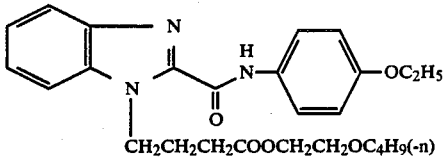

yellowish oil

Analysis: $C_{26}H_{33}N_3O_5$ (467.5).
Calculated: C 66.8; H 7.07; N 8.99; O 17.13, Found: C 66.4; H 7.3; N 9.0 ; O 17.5.

EXAMPLE 36

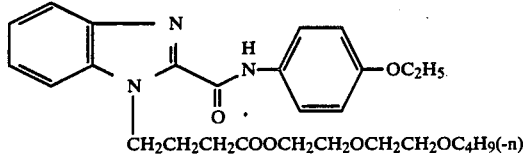

yellowish oil.

Analysis: $C_{28}H_{37}N_3O_6$ (511.6).
UV($CH_2Cl_2$): $\lambda_{max}$ ($\epsilon \cdot 10^{-3}$) = 312 nm (23.0).

EXAMPLES 37-45

Transesterification with polyethylene glycols as described in Example 31 gives the following polyethylene glycol esters of the corresponding benzimidazole-1-carboxylic acids, which are isolated in the form of pale yellow resins or oils by the method described in Example 31. According to $^1$H-NMR analysis, these compounds are present almost exclusively as monoesters of the following formula:

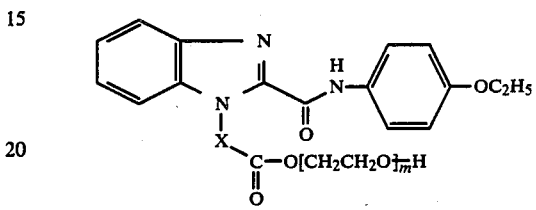

| Ex. | x | Average molecular weight of polyglycol | Analytical values found | | | |
|---|---|---|---|---|---|---|
| | | | C | H | N | O |
| 37 | $CH_2$ | 200 $\overline{m}$ = 4.5 | 60.8 | 6.7 | 8.2 | 24.9 |
| 38 | $(CH_2)_2$ | 200 | 62.1 | 6.6 | 8.5 | 23.5 |
| 39 | $(CH_2)_3$ | 200 | 61.7 | 6.8 | 7.8 | 23.9 |
| 40 | $CH_2$ | 300 $\overline{m}$ = 6.8 | 60.0 | 6.8 | 7.3 | 26.2 |
| 41 | $(CH_2)_2$ | 300 | 60.7 | 6.9 | 7.2 | 25.1 |
| 42 | $(CH_2)_3$ | 300 | 61.0 | 7.2 | 6.9 | 25.2 |
| 43 | $CH_2$ | 400 $\overline{m}$ = 9.1 | 59.1 | 7.1 | 6.2 | 27.6 |
| 44 | $(CH_2)_2$ | 400 | 59.9 | 7.3 | 6.3 | 26.9 |
| 45 | $(CH_2)_3$ | 400 | 60.4 | 7.4 | 6.3 | 26.6 |

EXAMPLE 46

35.3 g of 1-carbomethoxymethyl-4'-ethoxybenzimidazole-2-carboxanilide (compound of Example 4) are heated together with 130 ml of cyclohexylamine under nitrogen at 130° C. for 2.5 hours, during which the methanol formed is distilled off. After cooling down, 250 ml of methanol are added to dilute the mixture, and the precipitated product is filtered off with suction and washed with methanol, leaving 20.3 g of a colorless solid of the formula

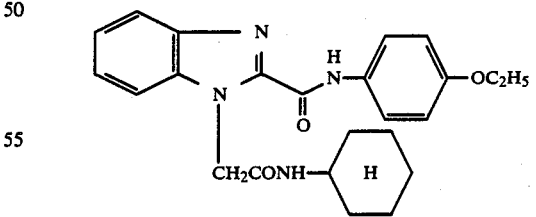

of melting point 239° C.

Analysis: $C_{24}H_{28}N_4O_3$ (420.3).
Calculated: C 68.54; H 6.7; N 13.3; O 11.42. Found: C 68.7; H 6.9; N 13.2; O 11.2.
UV($CH_2Cl_2$): $\lambda_{max}$ ($\epsilon \cdot 10^{-3}$) = 314 nm (19.6).

EXAMPLE 47

Example 46 is repeated with benzylamine, affording a product of the formula

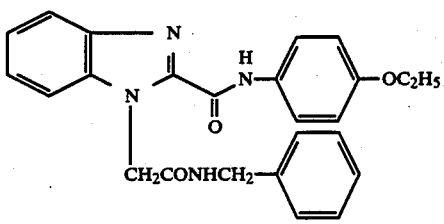

of melting point 198°–200° C.
Analysis: $C_{25}H_{24}N_4O_3$ (428.5).
Calculated: C 70.09; H 5.61; N 13.08; O 11.22. Found: C 70.4; H 5.8; N 13.2; O 10.8.

EXAMPLE 48

Example 46 is repeated using aniline in place of cyclohexylamine. The result is the 1-carboxyanilidomethylbenzimidazole of the formula

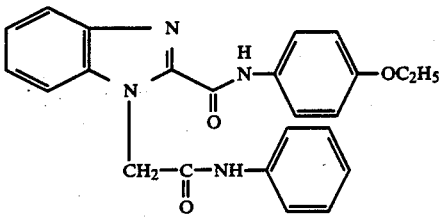

of melting point 246°–248° C.
Analysis: $C_{24}H_{22}N_4O_3$ (414.3).
Calculated: 69.57; H 5.32; N 13.52; O 11.59, Found: C 69.61; H 5.4; N 13.4; O 11.4.

EXAMPLE 49

35.3 g of 1-carbomethoxymethyl-4'-ethoxybenzimidazole-2-carboxanilide (compound of Example 4) are stirred in 70 ml of 3-(2-ethylhexoxy)propylamine at 135°–140° C. for 4.5 hours. The reaction mixture is cooled down to about 80° C. and poured in 1000 ml of methanol. 600 ml of ice-water are slowly added to precipitate the product, which is filtered off with suction and washed with water. The residue obtained is once more dissolved in 500 ml of methanol by heating, treated with active charcoal and reprecipitated by addition of 600 ml of ice-water. Filtering off with suction, washing and drying leaves 43.0 g of a colorless solid of the formula

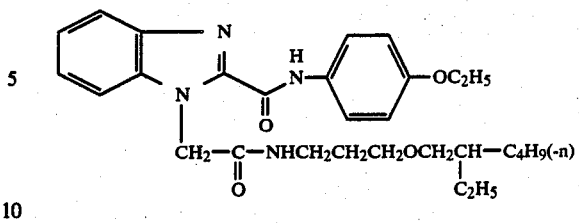

of melting point 140°–141° C.
Analysis: $C_{29}H_{40}N_4O_4$ (508.7).
Calculated: C 68.50; H 7.88; N 11.02; O 12.6. Found: C 68.2; H 8.0; N 10.9; O 12.2.

EXAMPLE 50

Example 49 is repeated reacting 1-carbomethoxyethyl-4'-ethoxybenzimidazole-2-carboxanilide (from Example 5) with 3-(2-ethylhexoxy)propylamine. The result is the compound of the formula

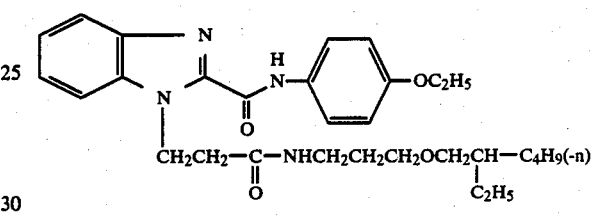

of melting point 118°–119° C.
Analysis: $C_{30}H_{42}N_4O_4$ (522.7).
Calculated: C 68.9; H 8.05; N 10.73; O 12.26. Found: C 69.1; H 8.2; N 10.6; O 12.3.

EXAMPLE 51

The method of Examples 49 and 50 is followed to prepare froml-carbomethoxypropyl-4'-ethoxybenzimidazole-21-carboxanilide (from Example 6) the compound of the formula

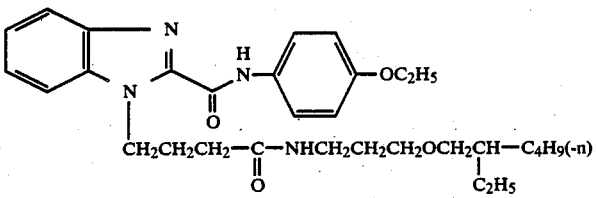

of melting point 108°–110° C.
Analysis: $C_{31}H_{44}N_4O_4$ (536.8).
Calculated: C 69.40; H 8.22; N 10.44; O 11.94, Found: C 69.2; H 8.4; N 10.3; O 11.91.

EXAMPLE 52

57.2 g of 1-carbomethoxypropyl-4'-ethoxybenzimidazole-2-carboxanilide (compound of Example 6) and g of p-toluenesulfonic acid are stirred in 230 ml of isodecanol at 140° C. for 3 hours. The hot reaction mixture is poured into 1 l of ice-water, and the resulting mixture is subsequently extracted with 500 ml of ethyl acetate. The organic phase is washed twice with 500 ml of water and then purified with active charcoal and bleaching earth. The solvent is distilled off under reduced pressure, leaving 69 g of a slightly yellow oil which corresponds to the product of the formula

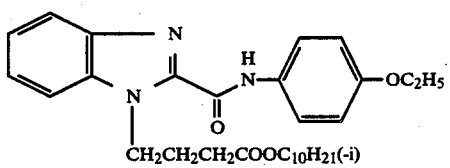

$C_{30}H_{41}N_3O_4$ (509.4).

UV ($CH_2Cl_2$): $\lambda_{max} \cdot (\epsilon \cdot 10^{-3}) = 313$ nm (20.8).

EXAMPLE 53

26.2 g of thionyl chloride are added dropwise to a suspension of 73.4 g of 1-(3-carboxypropoxypropyl)-4'-ethoxybenzimidazole-2-carboxanilide (compound of Example 3) and 400 ml of n-butyltriglycol at from $-5°$ to $0°$ C. The reaction mixture is stirred at room temperature for 0.5 hours and at 80° C. for 2.5 hours and is then discharged onto 1.5 l of ice-water. The mixture is brought to pH 7-8 with $NaHCO_3$ and extracted 3 times with 500 ml of ethyl acetate. The combined organic phases are washed with 500 ml of water, and dried over $Na_2SO_4$ and purified by means of active charcoal and bleaching earth. Concentrating under reduced pressure leaves 105 g of a yellowish oil corresponding to the product of the formula

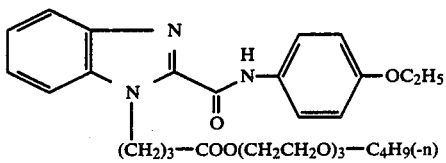

$C_{30}H_{41}N_3O_4$ (555.3).

UV ($CH_2Cl_2$) : $\lambda_{max} \cdot (\epsilon \cdot 10^{-3}) = 313$ nm (19.1).

EXAMPLE 54

38.1 g of the product of Example 6 are heated in 100 ml of n-octylamine at 140°-145° C. for 7.5 hours. After about 20 ml of n-octylamine have been distilled off, 700 ml of naphtha are added to the reaction mixture, and the resulting precipitate is filtered off with suction, washed with naphtha and dried, leaving 41.4 g of the compound of the formula

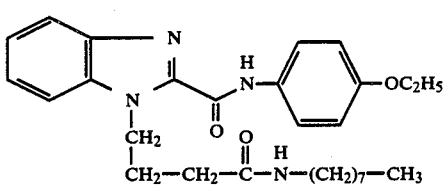

a colorless solid of melting point 137°-138° C.

Analysis: $C_{28}H_{38}N_4O_3$ (478.3).

Calculated: C 70.25; H 8.0; N 11.71; O 10.03, Found: C 70.1; H 8.3; N 11.8; O 10.2.

EXAMPLE 55

30.5 g of the product of Example 6 are heated in 100 ml of oleylamine at 140°-145° C. for 13 hours. After cooling down to 70° C., the reaction mixture is poured into 800 ml of methanol, and the mixture is stirred for 1 hour. The resulting precipitate is filtered off with suction, washed with methanol and dried at 50° C. under reduced pressure, leaving 25.5 g of a compound of the formula

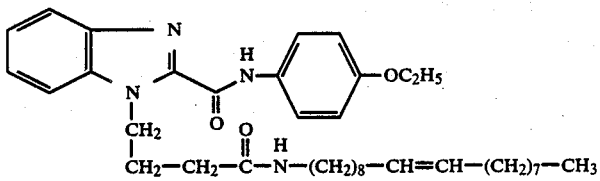

of a colorless solid of melting point 114°-116° C.

EXAMPLE 57

Thionyl chloride is added dropwise to a solution of 18.4 g of the product of Example 5 and 14.2 g of di-n-butylamine in 180 ml of toluene at 10°-15° C. After 1.5 hours at 40° C. and 6 hours at 80° C. the reaction mixture is poured onto a mixture of 300 ml of ice-water and 100 ml of 10% strength hydrochloric acid. The organic phase is separated off and extracted with 300 ml of 10% strength hydrochloric acid and then with saturated sodium bicarbonate solution. The organic phase is decocted twice for 1 hour with 7.5 g of active charcoal and 7.5 g of bleaching earth each time. After filtration, the solvent is distilled off under an aspirator vacuum, and the residue is recrystallized from 450 ml of naphtha. Filtering off with suction and drying leaves 13.3 g of the compound of the formula

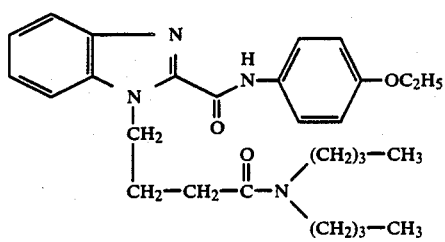

as a colorless solid of melting point 78°-80° C.

EXAMPLES 58 BIS 64

By reacting the product of Example 3 with amines and thionyl chloride in toluene by the method of Example 57, amides of the following formula are obtained:

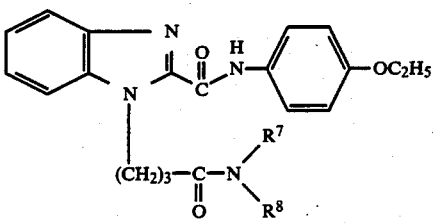

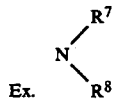

| Ex. | $R^8$ | Mp. (°C.) | Analysis |
|---|---|---|---|
| 58 | N—[CH₂—CH(C₂H₅)—(CH₃)₃—CH₃]₂ | oil | calcd. C 73.2 H 9.2 N 9.5 O 8.1<br>found C 72.5 H 9.1 N 9.1 O 8.9 |
| 59 | (morpholine ring) N  O | 115–117 | calcd. C 66.0 H 6.4 N 12.8 O 14.7<br>found C 65.5 H 6.7 N 12.4 O 15.5 |
| 60 | (piperidine ring) N | 48–52 | calcd. C 69.1 H 7.0 N 12.9 O 11.0<br>found C 68.5 H 7.3 N 12.4 O 11.7 |
| 61 | H N—(cyclopentyl) | 185–186 | calcd. C 69.1 H 7.0 N 12.9 O 11.0<br>found C 69.1 H 7.2 N 13.0 O 11.1 |
| 62 | H<br>N—CH₂—CH(CH₃)₂ | 181 | |
| 63 | H<br>N—CH(CH₃)—CH₂—CH₃ | 160 | |
| 64 | H<br>N—(CH₂)₃—CH₃ | 149 | |

(B) Application Examples

APPLICATION EXAMPLE 1

(Light-stabilizing action in polyurethane)

Preparation of polyurethane samples for irradiation tests

A polyol component composed of 41.9 parts of a polyetherol of OH number 29.0, obtained by addition of propylene oxide and ethylene oxide onto propylene glycol and having approximately 84% of primary hydroxyl groups, and 42.5 parts of a polyetherol of OH number 27.0, obtained by addition of propylene oxide and ethylene oxide onto trimethylolpropane and having approximately 88% of primary hydroxyl groups, and 8.1 parts of 1,4-butanediol and 1.724 parts of a 25% strength solution of diazabicyclooctane in 1,4-butanediol and 0.016 part of dibutyltin dilaurate and 0.1 part of the silicone stabilizer OS 710 from Bayer and 5.49 parts of Frigen 11 and 0.17 part of water was admixed with the stated stabilizers and foamed in a mixing ratio of 100:48.5 with a prepolymer having an isocyanate group content of 23.0% at a component and mold temperature of 25° C. to form test sheets. The NCO prepolymer was prepared from 87.17 parts of 4,4'-diphenylmethane diisocyanate and 4.83 parts of a polyetherol of OH number 250, obtained by addition of propylene oxide onto propylene glycol, and 8.0 parts of dipropylene glycol.

The samples were irradiated in a Xenotest ® 450 and rated in terms of the yellowness index (YI) of ASTM D 1925. The results are given in Table 2.

TABLE 2

| Stabilizer | Concentration [%] | YI of ASTM D 1925 | |
|---|---|---|---|
| | | 0 h | 96 h |
| 2.1  0 (control) | — | 1.4 | 31.7 |

TABLE 2-continued

| Stabilizer | | Concentration [%] | YI of ASTM D 1925 0 h | 96 h |
|---|---|---|---|---|
| 2.2 | 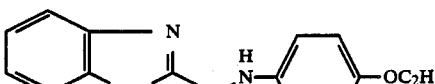 (Example 9) | 1.0 | 1.9 | 15.6 |
| 2.3 | 2-(2'-Hydroxy-5'-methyl-phenyl)benzotriazole | 0.5 | 2.7 | 23.2 |
| | +A* | 0.5 | | |
| | +Triethylene glycol bis-3-(3-t-butyl-4-hydroxy-5-methylphenyl)propionate | 0.25 | | |

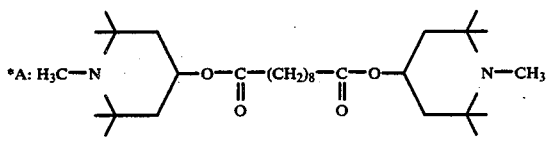

APPLICATION EXAMPLE 2

The following samples listed in Table 3 were prepared and tested as described in Application Example 1:

TABLE 3

| Stabilizer | | Concentration [%] | YI of ASTM D 1925 0 h | 96 h |
|---|---|---|---|---|
| 3.1 | 0 (control) | — | 5.0 | 32.5 |
| 3.2 | Compound of Example 27 | 0.5 | 4.2 | 21.1 |
| | + A | 0.5 | | |
| | + B(**) | 0.25 | | |
| 3.3 | Compound of Example 19 | 0.5 | 5.9 | 20.6 |
| | + A | 0.5 | | |
| | + B(**) | 0.25 | | |
| 3.4 | Compound of Example 28 | 0.5 | 5.0 | 22.8 |
| | + A | 0.5 | | |
| | + B(**) | 0.25 | | |
| 3.5 | Compound of Example 10 | 0.5 | 3.2 | 16.2 |
| | + A | 0.5 | | |
| | + B | 0.25 | | |

(**) B:mixture of 1 part by weight of α-tocopherol and 10 parts by weight of tris(nonylphenyl) phosphite

APPLICATION EXAMPLE 3

The samples listed in Table 4 were prepared and irradiated by the method described in Application Example 1. Each sample was stabilized with mixtures of 0.5% of Uv absorber, 0.5% of sterically hindered amine (compound A of Application Example 1) and 0.25% of antioxidant (triethylene glycol bis-3-(3-t-butyl-4-hydroxy-5-methylphenyl)propionate).

TABLE 4

| UV absorber | YI of ASTM D 1925 after 0 h | after 96 h |
|---|---|---|
| 4.1 Unstabilized sample | 9.6 | 55.5 |
| 4.2 Compound of Example 37 | 5.7 | 22.4 |
| 4.3 Compound of Example 31 | 6.3 | 21.9 |
| 4.4 Compound of Example 39 | 5.5 | 18.3 |
| 4.5 Compound of Example 40 | 6.8 | 22.4 |
| 4.6 Compound of Example 42 | 5.0 | 21.7 |
| 4.7 Compound of Example 44 | 5.6 | 21.5 |
| 4.8 C*** | 5.7 | 21.7 |

***C: reaction product of 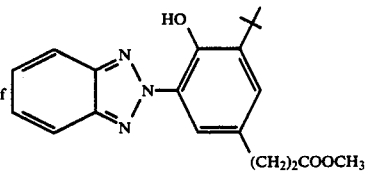 with a polyethylene glycol of average molecular weight 300.

APPLICATION EXAMPLE 4

Volatility Of Stabilizers In The Clear Coat Of A Two-Coat Metallic System 0.4 g of each of the stabilizers indicated in Table 5 are stirred into 55.6 g of a ready-to-spray clear coating formulation, comprising 1500 parts of acrylate baking finish and 167 parts of xylene, until completely dissolved.

The ready-prepared coating solution is drawn down on a piece of quartz glass (thickness about 40 μm) and baked at 140° C. for 5 hours. To determine the loss of Uv absorber during baking, absorption spectra are recorded before and after baking, and the loss is determined from the decrease in the optical density at the absorption maximum.

TABLE 5

| Stabilizer | Percentage loss after 5 h at 140° C. |
|---|---|
| 5.1 Compound of Example 6 | 7 |
| 5.2 Compound of Example 20 | 5 |
| 5.3 Compound of Example 25 | 6.3 |
| 5.4 Compound of Example 32 | 2.7 |
| 5.5 Compound of Example 34 | 3.7 |
| 5.6 Compound of Example 36 | 5 |
| 5.7 Compound of Example 39 | 4 |
| 5.8 Compound of Example 40 | 4 |
| 5.9 Compound of Example 42 | 4 |
| 5.10 Compound of Example 51 | 6 |

We claim:
1. A compound of the formula I

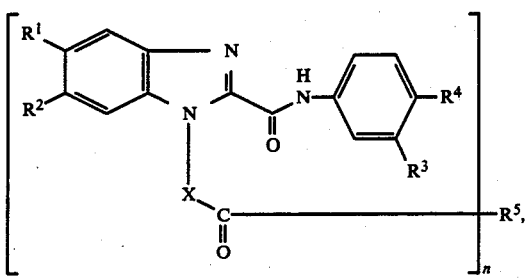

where
R$^1$ and R$^2$ are each independently of the other H, Cl, C$_1$-C$_4$-alkyl, C$_1$-C$_4$-alkoxy, unsubstituted or C$_1$-C$_4$-alkyl- or C$_1$-C$_4$-alkoxy-substituted phenyl or C$_7$-C$_9$-phenalkyl,
R$^3$ and R$^4$ are each independently of the other H, C$_1$-C$_{18}$-alkyl, C$_3$-C$_{18}$-alkyl which is interrupted one or more times by —O—, C$_1$-C$_{18}$-alkoxy, C$_4$-C$_{18}$-alkoxy which is interrupted one or more times by —O—, unsubstituted or C$_1$-C$_4$-alkyl- or C$_1$-C$_4$-alkoxy-substituted phenyl, C$_7$-C$_{15}$-phenylalkyl, phenoxy, C$_7$-C$_{15}$-phenylalkyloxy, C$_1$-C$_4$-hydroxyalkyl, C$_1$-C$_4$-hydroxyalkoxy, C$_1$-C$_{12}$-alkylcarbonylamino, C$_1$-C$_{12}$-alkanoyloxy, benzoylamino or benzoyloxy,
X is C$_1$-C$_5$-alkylene,
n is 1 and
R$^5$ is —when —Cl,

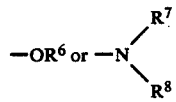

where
R$^6$ is H, unsubstituted or OH-monosubstituted, -disubstituted or -trisubstituted or —O—COR$^9$-substituted C$_1$-C$_{18}$-alkyl, C$_3$-C$_{18}$-alkyl which is interrupted one or more times by —O— or —NR$^9$—, unsubstituted or OH-substituted C$_5$-C$_{12}$-cycloalkyl, unsubstituted or OH-substituted C$_2$-C$_{18}$-alkenyl, C$_7$-C$_{15}$-phenylalkyl, phenoxyethyl,

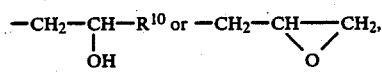

R$^7$ and R$^8$ are each independently of the other H, C$_1$-C$_{18}$-alkyl, C$_3$-C$_{18}$-alkyl which is interrupted one or more times by —O— or —NR$^9$—, C$_5$-C$_{12}$-cycloalkyl, phenyl, naphthyl, C$_3$-C$_{18}$-alkenyl, C$_7$-C$_{15}$-phenylalkyl, C$_2$-C$_4$-hydroxyalkyl or

is pyrrolidinyl, piperidinyl, piperazinyl or morpholinyl,
R$^9$ is H, C$_1$-C$_{18}$-alkyl, C$_5$-C$_{12}$-cycloalkyl, C$_3$-C$_8$-alkenyl, phenyl, naphthyl or C$_7$-C$_{18}$-phenylalkyl,
R$^{10}$ is H, C$_1$-C$_{18}$-alkyl, C$_7$-C$_{18}$-phenylalkyl, unsubstituted or substituted phenyl or —CH$_2$OR$^{11}$,
R$^{11}$ is C$_1$-C$_{18}$-alkyl, C$_3$-C$_{18}$-alkenyl, C$_5$-C$_{10}$-cycloalkyl, phenyl or C$_7$-C$_{15}$-phenylalkyl.
2. A compound as claimed in claim 1, wherein R$^1$ and R$^2$ are each independently of the other H, Cl, C$_1$-C$_4$-alkyl, C$_1$-C$_4$-alkoxy or C$_7$-C$_9$-phenylalkyl,
R$^3$ and R$^4$ are each independently of the other H, C$_1$-C$_{12}$-alkyl, C$_1$-C$_{12}$-alkoxy, C$_3$-C$_{10}$-alkyl which is interrupted one or more times by —O—, C$_3$-C$_{10}$-alkoxy which is interrupted one or more times by —O—, C$_7$-C$_9$-phenylalkyl, C$_7$-C$_9$-phenylalkoxy, phenoxy, C$_1$-C$_{12}$-alkylcarbonyloxy, benzoyloxy, C$_1$-C$_{12}$-alkylcarbonylamino or benzoylamino, and
X is C$_1$-C$_5$-alkylene.
3. A compound as claimed in claim 2, wherein
n is 1 and
R$^5$ is

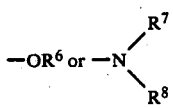

where
R$^6$ is H, C$_1$-C$_{18}$-alkyl which may be substituted by —OH or —OCOR$^9$, C$_3$-C$_{18}$-alkyl which is interrupted one or more times by —O— and which may in addition be OH-substituted, unsubstituted or OH-substituted C$_7$-C$_{12}$-cycloalkyl or C$_2$-C$_{18}$-alkenyl, C$_7$-C$_{15}$-phenylalkyl, phenoxyethyl,

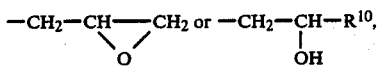

R$^7$ and R$^8$ are each independently of the other H, C$_1$-C$_{12}$-alkyl, C$_3$-C$_{18}$-alkyl which is interrupted one or more times by —O— or —NR$^9$—, C$_5$-C$_{12}$-cycloalkyl, unsubstituted or C$_1$-C$_6$-alkyl- or C$_1$-C$_6$-alkoxy-substituted phenyl, C$_7$-C$_{15}$-phenylalkyl or C$_2$-C$_4$-hydroxyalkyl or

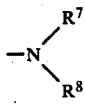

is a pyrrolidine, piperidine, piperazine or morpholine radical,
R$^9$ is H, C$_1$-C$_4$-alkyl, C$_5$-C$_{12}$-cycloalkyl, phenyl or benzyl,
R$^{10}$ is H, C$_1$-C$_{12}$-alkyl or —CH$_2$OR$^{11}$ and
R$^{11}$ is C$_1$-C$_{12}$-alkyl, C$_5$-C$_{10}$-cycloalkyl, phenyl or C$_7$-C$_9$-phenylalkyl.
4. A compound as claimed in claim 1, wherein
R$^1$ and R$^2$ are each independently of the other H, Cl, methyl, ethyl, methoxy, ethoxy, benzyl, methylbenzyl or α,α-dimethylbenzyl,
R$^3$ and R$^4$ are each independently of the other H, C$_1$-C$_6$-alkyl, C$_1$-C$_8$-alkoxy, C$_7$-C$_9$-phenylalkyl, C$_7$-C$_9$-phenylalkoxy, phenoxy, benzoyloxy, C$_1$-C$_8$-alkanoyloxy, C$_1$-C$_6$-alkanoylamino or benzoylamino,
X is C$_1$-C$_5$-alkylene,
n is 1 and
R$^5$ is —OR$^6$ or

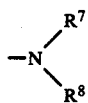

where
R$^6$ is H, C$_1$–C$_{18}$-alkyl, C$_3$–C$_{18}$-alkyl which is interrupted one or more times by —O— and which may in addition —OH-substituted, C$_5$–C$_{12}$-cycloalkyl, OH-substituted C$_5$–C$_{12}$-cycloalkyl, C$_2$–C$_{18}$-alkenyl, C$_7$–C$_9$-phenylalkyl, phenoxyethyl,

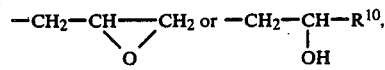

one of the radicals
R$^7$ and R$^8$ is H and the other is C$_1$–C$_{12}$-alkyl, C$_3$–C$_{18}$-alkyl which is interrupted one or more times by —O— or —NR$^9$—, C$_5$–C$_{12}$-cycloalkyl, unsubstituted or C$_1$–C$_6$-alkyl or C$_1$–C$_6$-alkoxy-substituted phenyl, C$_9$-phenylalkyl or C$_2$–C$_4$-hydroxyalkyl,
R$^9$ is H or C$_1$–C$_4$-alkyl,
R$^{10}$ is H, C$_1$–C$_{12}$-alkyl or —CH$_2$OR$^{11}$ and
R$^{11}$ is C$_1$–C$_{12}$-alkyl, C$_2$–C$_4$-alkenyl, cyclohexyl, phenyl or C$_7$–C$_9$-phenylalkyl.

* * * * *